United States Patent
Goetzelmann

[19]

[11] Patent Number: 5,934,859
[45] Date of Patent: Aug. 10, 1999

[54] DEVICE FOR HANDLING OBJECTS DISPOSED IN A PACKAGING CONTAINER

[75] Inventor: Bernd Goetzelmann, Rot Am See, Germany

[73] Assignee: Robert Bosch GmbH, Stuttgart, Germany

[21] Appl. No.: 08/930,788

[22] PCT Filed: Jan. 29, 1997

[86] PCT No.: PCT/DE97/00156

§ 371 Date: Oct. 6, 1997

§ 102(e) Date: Oct. 6, 1997

[87] PCT Pub. No.: WO97/29015

PCT Pub. Date: Aug. 14, 1997

[30] Foreign Application Priority Data

Feb. 6, 1996 [DE] Germany ............................ 196 04 100

[51] Int. Cl.$^6$ ................................ B65B 3/00; B65G 47/90
[52] U.S. Cl. ..................... 414/416; 294/81.52; 294/87.1; 414/736
[58] Field of Search .................................. 414/403, 416, 414/732, 736; 294/67.32, 81.52, 87.1; 53/247, 475

[56] References Cited

U.S. PATENT DOCUMENTS

| | | | |
|---|---|---|---|
| 3,024,058 | 3/1962 | Sinclair | 294/81.52 X |
| 3,081,124 | 3/1963 | Kaplan | 294/87.1 |
| 3,797,683 | 3/1974 | Simpatico | 414/416 X |
| 4,162,018 | 7/1979 | Arya | 414/416 X |
| 4,383,795 | 5/1983 | Wakamatsu et al. | 294/87.1 X |
| 4,384,739 | 5/1983 | Gustavsson et al. | 294/67.32 X |
| 4,778,329 | 10/1988 | Phillips | 414/732 X |
| 4,975,018 | 12/1990 | Langenbacher et al. | 294/67.32 X |
| 5,290,134 | 3/1994 | Baba | 414/416 X |
| 5,471,738 | 12/1995 | Burcham et al. | 294/87.1 X |

OTHER PUBLICATIONS

U.S. Patent No. 4,374,559 to Morton dated Feb. 22, 1983.
U.S. Patent No. 4,505,636 to Sugino et al dated Mar. 19, 1985.
EP No. 0 257 230 to R. Haarer dated June 24, 1987.
German Offenlegungsschrift 27 35 279 Apr. 1978.
German Offenlegungsschrift DE 44 12 417 A1 Oct. 1994.
Swiss Patent No. 462 711 Oct. 1968.
Swiss Patent No. 582 089 Nov. 1976.

*Primary Examiner*—James W. Keenan
*Attorney, Agent, or Firm*—Edwin E. Greigg; Ronald E. Greigg

[57] ABSTRACT

A device for handling syringe bodies stored in trays. The device has a transfer unit for the syringe bodies and a movable matrix that cooperates with it. Recesses for the syringe bodies are embodied in the transfer unit. To secure the syringe bodies in the recesses, the transfer unit has pins that are supported so they can rotate and are provided with securing catches. To press the tray away from the syringe bodies, in one embodiment of the invention, a number of press struts are disposed on the matrix. The device according to the invention has the advantage that the handling of the syringe bodies occurs very gently. Furthermore, the device can advantageously be coupled to a handling robot.

16 Claims, 8 Drawing Sheets

DEVICE FOR HANDLING OBJECTS DISPOSED IN A PACKAGING CONTAINER

PRIOR ART

The invention relates to a device for handling objects disposed in a packaging container as has been disclosed, for example, by EP 0 257 230 A1.

There are mainly two types of packaging containers currently used for the storage and transport of syringe bodies. On the one hand, these are so-called trays that are thermoformed containers in which a large number of ribs with tray nubs formed into them, between which a syringe body is respectively disposed with positive engagement and with frictional, non-positive engagement. To fill the syringe bodies, for example with a medication, the syringe bodies must be removed from the tray, supplied first to a cleansing and sterilizing device and then to a filling and closing device. Then, the filled and closed syringe bodies are inserted back into the tray.

Furthermore, so-called SCF systems are known. An SCF system is understood to be a sterile packaged empty syringe unit. It is comprised of a tub-shaped plastic box, a covering mat, a rectangular tray, and the corresponding number of syringe bodies for this tray. Under sterile conditions, a protective foil is glued in an airtight manner to the plastic box, which is packaged in a plastic protective foil. In contrast to the simple tray mentioned first, with an SCF system, the syringe bodies are already sterilized at the manufacturer. As a result, the above-described cleansing and sterilizing of the syringe bodies is eliminated.

Since syringe bodies are objects that are mechanically sensitive depending on their embodiment, a device is desirable which permits a safe transport of the syringe bodies from their packaging container and into, for example, a cleansing and sterilizing device of a packaging machine and at the same time, puts as little as possible mechanical stress on the syringe bodies. In EP 0 257 230 A1, objects are in fact held in a mechanically gentle manner in the recesses by means of a vacuum, but the recesses must be very precisely adapted to the objects so that a sealed contact is produced between the objects and the suction bores. Moreover, the holding force is defined by the size of the suction bores and the magnitude of the vacuum so that the known device cannot be used with all syringe body formats.

ADVANTAGES OF THE INVENTION

The device according to the invention for handling objects disposed in a packaging container has the advantage that the syringe bodies are securely and at the same time, very gently transported and that it can be used for a wide range of formats.

Other advantages and advantageous embodiments of the device according to the invention for handling objects disposed in a packaging container ensue from the description set forth herein.

It is particularly advantageous to couple the transfer unit to a matrix. As a result, it is also possible to withdraw the syringe bodies from the tray and reintroduce them into it in a way that is gentle to both the syringe bodies and the tray.

In another preferred embodiment of the invention, the device is connected to an arm of a handling robot. As a result, the trays or the SCF system, before and after being filled with the syringe bodies, can be directly removed from storage or can be stored or stacked. The coupling of the device to a handling robot furthermore has the particular advantage that all of the geometrically dependent guides and drive members, which are necessary in the known devices, can be eliminated and that any arbitrary point within the range of the handling robot can be controlled. As a result, a great flexibility of the device is achieved.

BRIEF DESCRIPTION OF THE DRAWINGS

Two exemplary embodiments of the invention are represented in the drawings and are explained in detail in the following description.

DESCRIPTION OF THE EXEMPLARY EMBODIMENTS

Figure 1:
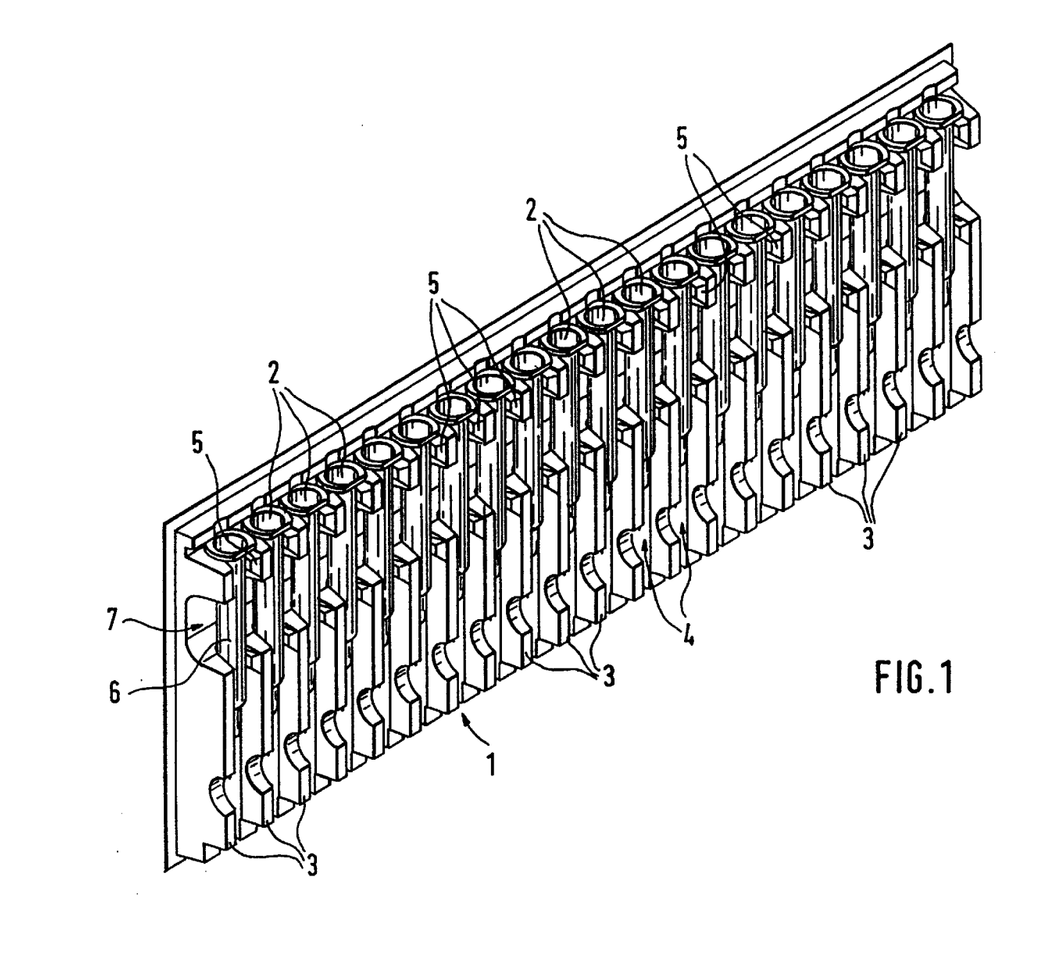
FIG. 1 is a perspective view of a tray filled with syringe bodies.

In the first exemplary embodiment of the invention, the device 10 is used to handle syringe bodies 2 disposed in so-called trays 1 (FIG. 1). The molded trays 1, which are known per se and are made of plastic, have ribs 3 between which the syringe bodies 2 are respectively disposed axially parallel in recesses 4. The syringe bodies 2 are secured in the tray 1 with positive engagement by means of tray nubs 5 formed onto the ribs 3. Longitudinal recesses 7 are embodied in the ribs 3 in the region in which the syringe bodies 2 have their hollow, cylindrical midsection 6.

As a rule a large number of syringe bodies 2, for example twenty pieces, are disposed in the above-described trays 1. The trays 1 are supplied in stacks to the packager, where the syringe bodies 2 are removed from the tray 1 with the aid of the device 10. Then the syringe bodies 2 are first supplied to a cleansing and sterilizing device, not shown, and then to a filling and closing device for the syringe bodies 2. After the syringe bodies 2 are filled and respectively closed with a closing stopper, the syringe bodies 2 are reintroduced into the tray 1.

Figure 2:
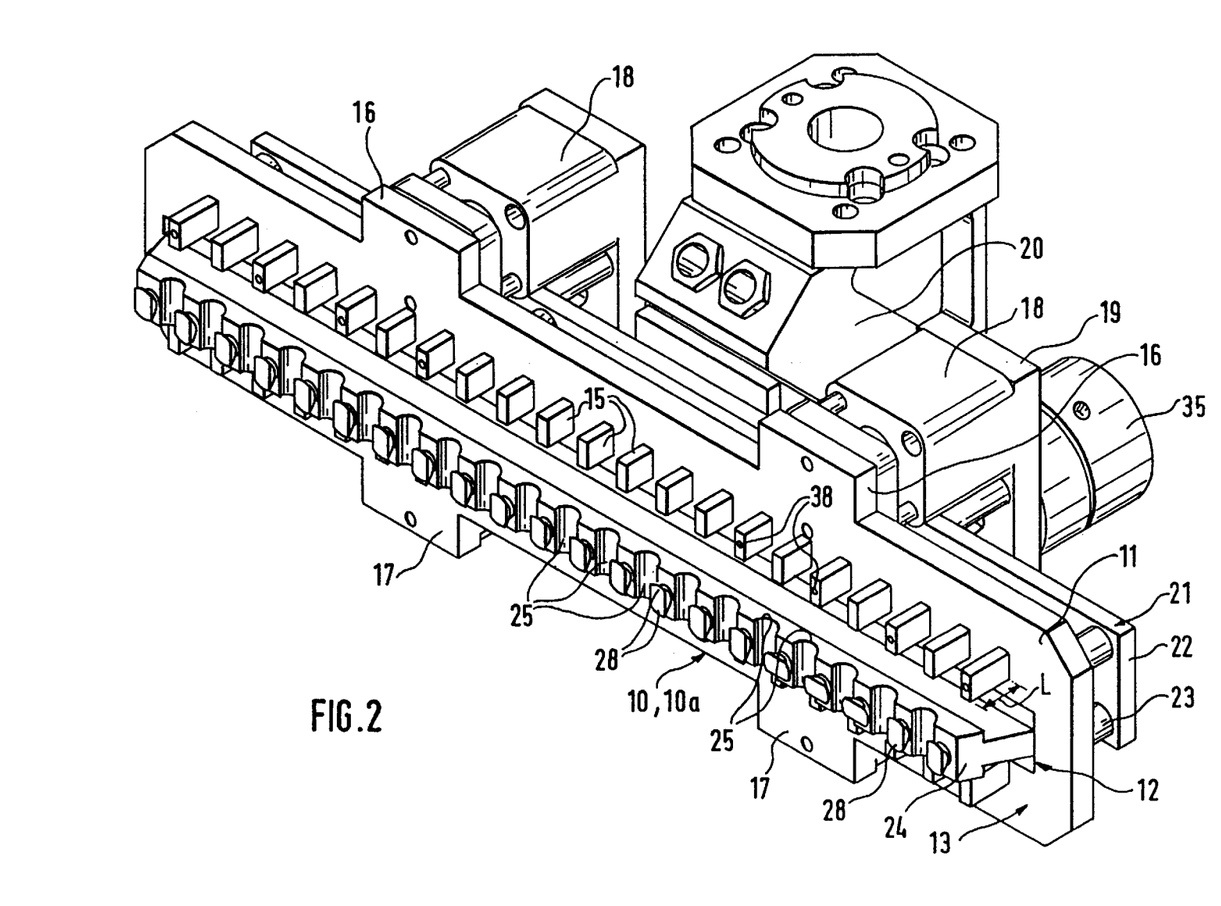
FIG. 2 is a perspective view of a device for handling objects disposed in a packaging container.

The device 10 has an essentially rectangular, plate-shaped matrix 11 with a longitudinal slot 12 embodied centrally in it (FIG. 2). Above and below the longitudinal slot 12, block-shaped press struts 15 for a tray 1 are attached to the front side 13 of the matrix 11. The disposition of the press struts 15 on the matrix 11 is done in such a way that they are disposed coinciding with the ribs 3 of the tray 1, wherein a press strut 15 is disposed above and below a longitudinal recess 7 of a rib 3. Furthermore, the length L of the press struts 15 varies, wherein the press struts 15 disposed in the lateral edge regions of the matrix 11 have a greater length L than the press struts 15 disposed in the central region of the matrix 11. As a result, in a top view of the matrix 11, a circular or arced contour of the press struts 15 is produced.

Two extensions 16, 17 are respectively formed onto the upper and lower end face of the matrix 11. A pneumatically operated lifting unit 18 is connected to each pair of extensions 16, 17, on the side of the matrix 11 opposite the press struts 15, wherein the two lifting units 18 are operated synchronously. The two lifting units 18 are connected to a common base carrier 19, which in turn is coupled to a pivoting and rotating device 20 disposed between the two lifting units 18.

A transfer unit 21 for the syringe bodies 2 is connected to the pivoting and rotating device 20. The transfer unit 21 is comprised of a plate 22 that is connected to the base carrier 19 and is connected by means of spacer sleeves 23 to a syringe body carrier 24 that has a horizontal parting plane. Independent of the lifting motion of the matrix 11, the plate 22 oriented toward the base carrier 19 is always disposed between the base carrier 19 and the matrix 11. The syringe body carrier 24 passes through the longitudinal slot 12 of the matrix 11.

Figure 3:
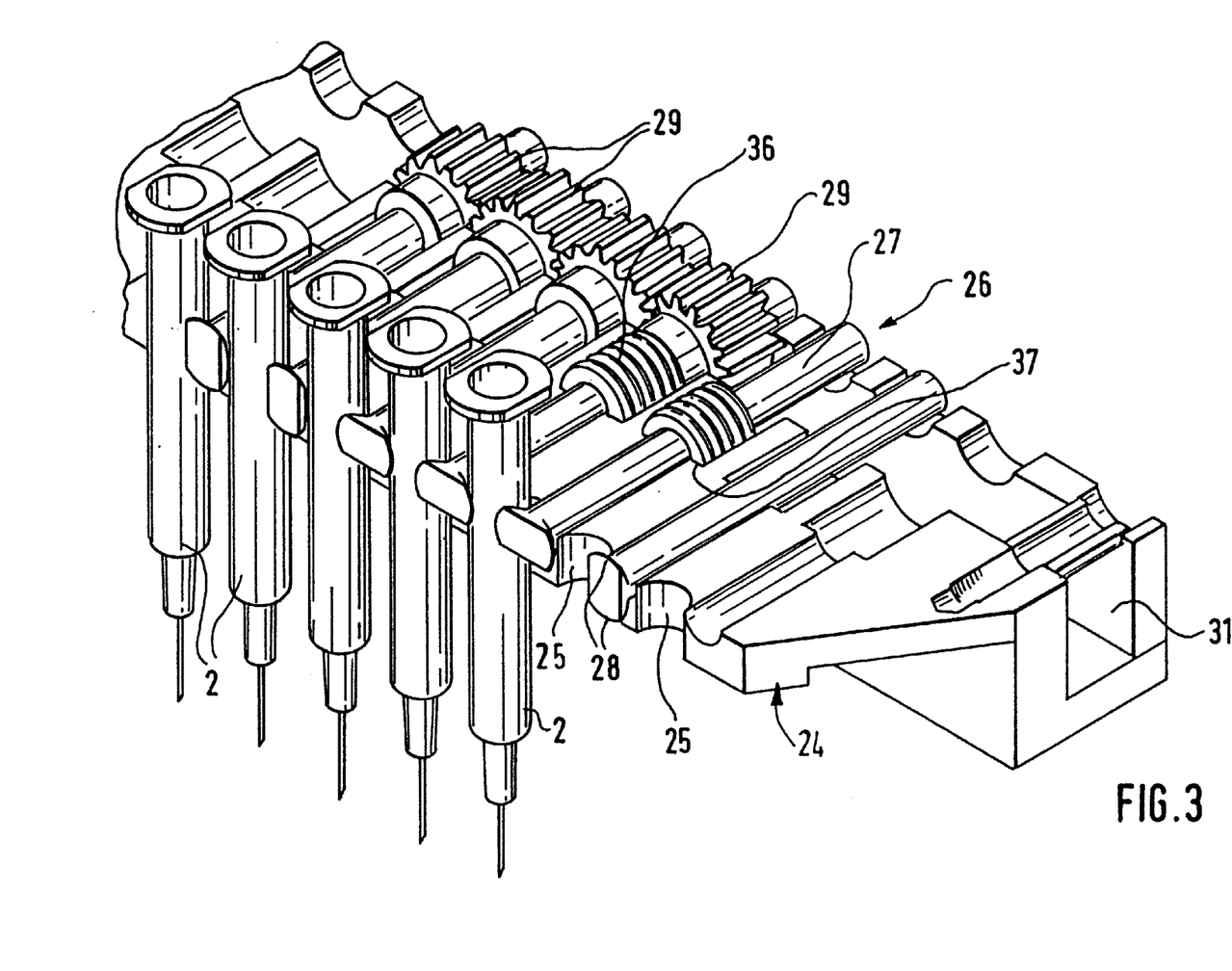
FIG. 3 is a perspective view of a part of the device according to FIG. 2, FIGS. 4 and 5 are side views of the device according to FIG. 2 during two operating phases.

As shown in FIG. 3, in the region between the upper and lower row of press struts 15, i.e. in the region of the longitudinal slot 12, the syringe body carrier 24 has recesses 25 that are adapted to the syringe bodies 2, which recesses are semicircular in the exemplary embodiment and cover approximately half the cross sectional area of the syringe bodies 2. Rotary closing elements 26 are disposed between the recesses 25 at the level of the recesses 25.

The closing elements 26 are respectively comprised of an essentially cylindrical pin 27 and two securing catches 28 for the syringe bodies 2 are formed onto this pin on its end face oriented toward the recesses 25. In the one end position of the pins 27, the securing catches 28 are aligned with the longitudinal axes of the syringe bodies 2 so that the recesses 25 are completely unblocked for the syringe bodies 2. In the other end position of the pins 27, which is rotated by 90 degrees, the securing catches 28 cover the openings of the recesses 25 at least partially so that a syringe body 2 disposed in a recess 25 is grasped with positive engagement by the recess 25 and the associated securing catches 28 of two pins 27.

A gear 29 is secured to the pin 27 in a non-rotating fashion on the opposite end from the securing catches 28 and is disposed in a recess 31 embodied in the syringe body carrier 24. The individual gears 29 of the pins 27 mesh with one another so that when one pin 27 turns, the other pins 27 are inevitably turned synchronously with it. In order to permit the rotary motion of the pins 27 between the two end positions, at least one of the pins 27 is elongated beyond its gear 29 and coupled to an adjusting motor 35 disposed in the region of the base carrier 19.

Between the securing catches and the gear 29, a compression spring 36 is associated with each pin 27; this spring is supported on one end against the pin 27 and on the other end against a shoulder 37 in the syringe body carrier 24, and presses the pin 27 and consequently also the securing catches 28 in the direction of the recess 25.

The above-described device 10 is suited for withdrawing the syringe bodies 2 from a tray 1. The reintroduction of (filled) syringe bodies 2 into empty trays 1 is carried out by means of a modified device 10a. This device 10a (FIG. 2) differs from the device 10 by virtue of the fact that blind bores 38 are embodied in a number of press struts 15, for example in eight press struts 15; these bores feed into the end faces of the press struts 15 oriented toward the ribs 3 of the tray 1, and are connected to a vacuum source, not shown.

Figure 6:
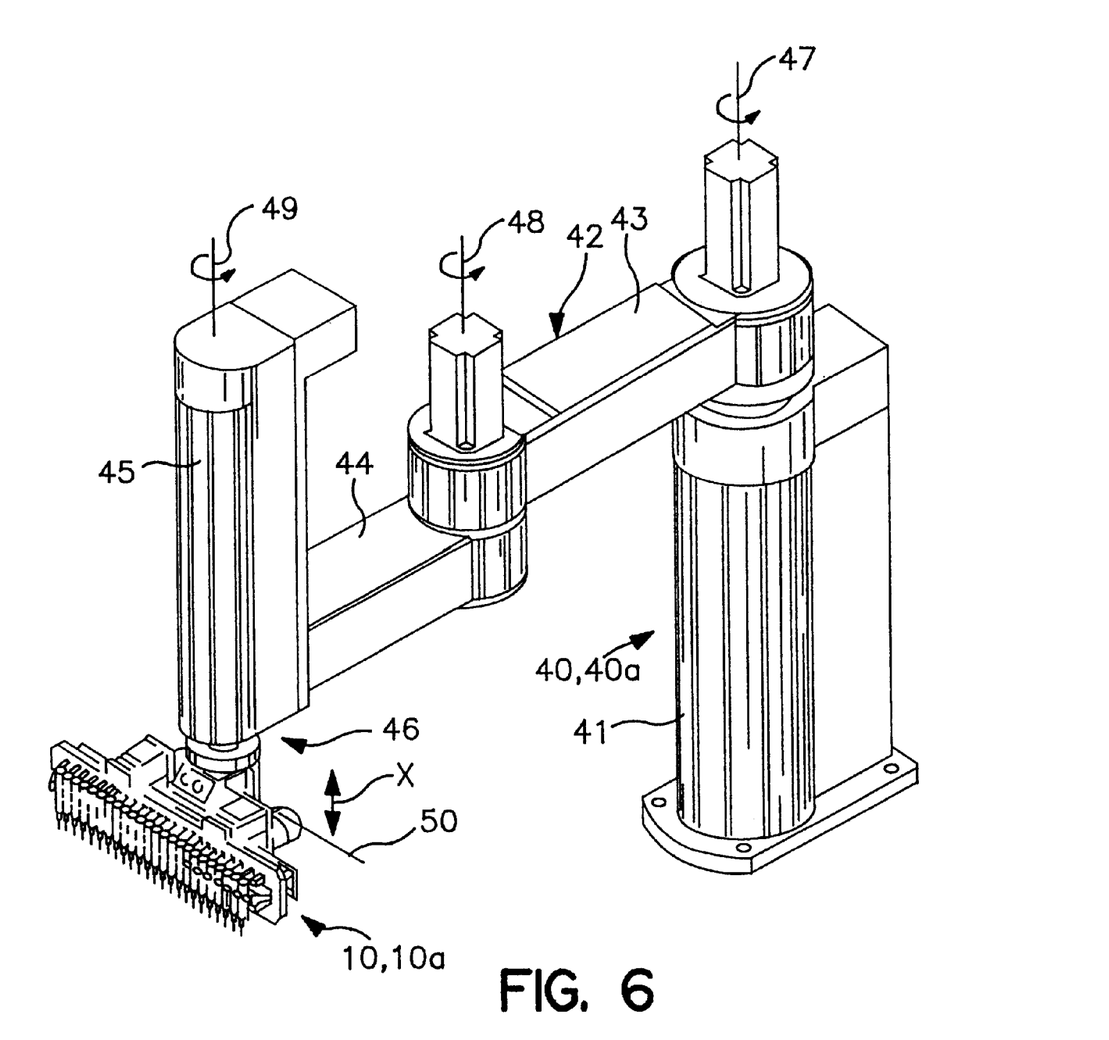
FIG. 6 is a perspective view of a handling system for objects.

Both the device 10 and the device 10a can be coupled to a handling robot 40 with their respective base carrier 20 (FIG. 6). The handling robot 40 has a stanchion 41 from which an arm 42 leads that has two sections 43, 44 articulatingly connected to each other, of which one section 44 is connected to a lifting unit 45. The device 10, 10a is connected to the bottom end 46 of the lifting unit 45 by means of the pivoting and rotating device 20. The handling robot 40 has a total of five degrees of freedom: the arm 42 can be rotated around the first vertical axis 47 in the stanchion 41. Furthermore, the two sections 43, 44 are supported so they can rotate around the second vertical axis 48. The third vertical axis 49 is realized by the rotary mobility of the device 10, 10a in the pivoting and rotating device 20. Furthermore, the device 10, 10a can be raised and lowered in the x direction by the lifting unit 45 and can be pivoted by the pivoting and rotating device 20 by at least 90 degrees around a horizontally disposed axis 50.

Figure 4:
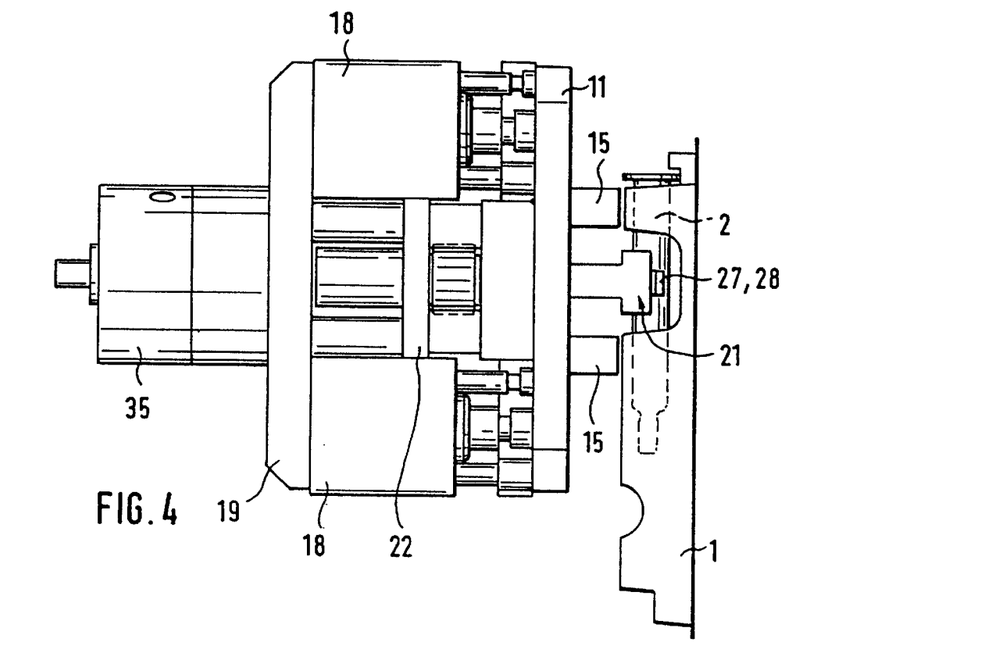

The above-described device 10, 10a for handling syringe bodies 2 functions as follows: the device 10 is mounted on the handling robot 40 in order to remove the syringe bodies 2 from a tray 1, which has been placed in readiness, for example in a stacked storage. Furthermore, the securing catches 28 are rotated into the one position unblocking the recesses 25 in the syringe body carrier 24, and by means of the lifting units 18, the matrix 11 is moved into the next position from the base carrier 19. In this starting adjustment of the device 10, the handling robot 40 is pivoted in the direction of the tray 1, wherein due to the degree of freedom of the handling robot 40, it is unimportant whether the tray 1 is disposed horizontally or vertically. The only condition is that the front side of the tray 1 associated with the syringe bodies 2 is freely accessible. After the recesses 25 of the syringe body carrier 24 are aligned to the syringe bodies 2 in the tray 1, the syringe body carrier 24 is slid into the tray 1 until the syringe bodies 2 come into contact with the recesses 25 of the syringe body carrier 24. In this position, the pins 27 are rotated by 90 degrees by means of the adjusting motor 35 so that the securing catches 28 of the pins 27 grasp the syringe bodies 2 (FIG. 4). Since the compression springs 36 press the securing catches 28 in the direction of the recesses 25, the syringe bodies 2 are held in the syringe body carrier 24 with positive engagement and with frictional, non-positive engagement.

The handling robot 40 now transports the device 10 together with the tray 1 and the syringe bodies 2 to a storage or collecting point for empty trays 1. The separation of the syringe bodies 2 from the tray 1 takes place there.

Figure 5:
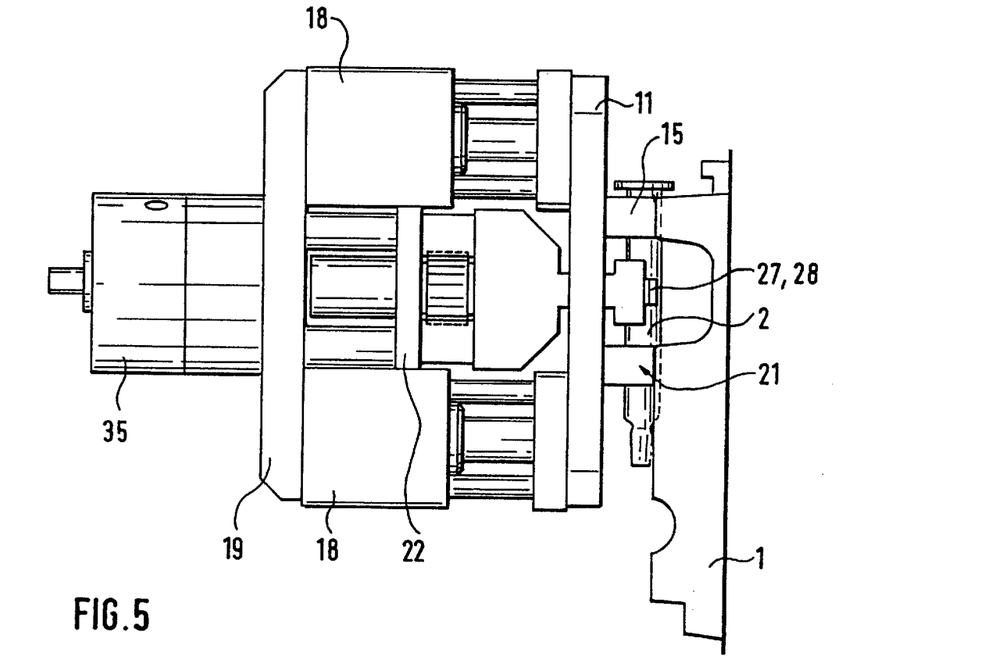

In order to remove the syringe bodies 2 from the tray 1, the matrix 11 is moved by means of the lifting units 18 in the direction of the recesses 25 of the syringe body carrier 24. As a result, the press struts 15 gradually come into contact with the ribs 3 of the tray 1 and press the tray 1 away from the syringe bodies 2 until they are released from the ribs 3 (FIG. 5). The release of the individual syringe bodies 2 occurs in a gradual manner corresponding to the different lengths L of the press struts 18, starting from the lateral edge zones of the matrix 11 and moving in toward its central region.

After the syringe bodies 2 have been removed from the tray 1, the handling robot 40 is moved farther with the syringe bodies 2 disposed in the syringe body carrier 24 and (after releasing the syringe bodies 2 by means of rotating the pins 27 back into their original position, which unblocks the recesses 25) transfers the syringe bodies 2 into a conveying device, not shown, which is known per se and functions in a continuous or cyclical manner. By means of the conveying device, the syringe bodies 2 are first supplied to a cleansing and sterilizing device and are then supplied to a filling and closing device for the syringe bodies 2, from which they are then released once again, and are supplied into the region of a second handling robot 40*a*. The device 10*a* in the exemplary embodiment represented is affixed to this second handling robot 40*a*. The transfer of the filled syringe bodies 2, which are closed by closing stopper means, in between the ribs 3 of an empty tray 1 is carried out by virtue of the fact that in a first work step, the conveying device introduces the syringe bodies 2 into the recesses 25 of the syringe body carrier 24. As soon as the syringe bodies 2 are disposed in the syringe body carrier 24 with positive engagement and frictional, non-positive engagement (after a corresponding rotation of the pins 27 into the end position that covers the recesses 25), the handling robot 40*a* pivots the device 10*a* into the region of a prepared empty tray 1. After the press struts 15 are aligned with the ribs 3 of tray 1, the press struts 15 are brought into contact with the associated ribs 3 of the tray 1. By switching on the vacuum source, the ribs 3 and consequently the tray 1 are subjected to suction via the suction bores 38, and are positioned opposite the syringe body carrier 24.

Then the handling robot 40*a* pivots the device 10*a* together with the tray 1 into the region of a stationary, smooth plate for the tray 1, which plate is preferably slightly inclined to the horizontal and is resiliently supported. This plate constitutes a countersupport for the matrix 11 for the subsequent insertion of syringe bodies 2 into the tray 1.

The insertion of the syringe bodies 2 between the ribs 3 of the tray 1 is carried out by virtue of the fact that (after the pivoting and rotating device 20 is pivoted around the horizontal axis 50) in order to set the tray 1 down on the plate, the vacuum with which the tray 1 had been held is switched off and the matrix 11 is backed away, i.e is moved in the direction of the base carrier 19. At the same time, the lifting unit 45 moves the device 10*a* in the direction counter to the slightly inclined tray 1 so that the syringe bodies 2 are gradually pressed between the tray nubs 5 of the ribs 3.

After the insertion of all the syringe bodies 2 between the ribs 3 of the tray 1 and the possible setting down of the now-filled tray 1 in another location by the handling robot 40*a*, the pins 27 are rotated by means of the adjusting motor 35 back into their end position that unblocks the recesses 25 so that the tray 1 is free.

In lieu of the above-described reinsertion of the syringe bodies 2 into the empty tray 1 by means of the device 10*a* and the smooth plate that functions as a countersupport, the reinsertion of the syringe bodies 2 is also conceivable using a device 10 that is simpler in terms of its design. In this instance, after the alignment with the empty tray 1, the syringe bodies 2 are inserted between the ribs 3 disposed under the syringe bodies 2 (tray 1 disposed flat). This is carried out by virtue of the fact that the vertical lift of the handling robot 40 is utilized in order to press the syringe bodies 2 between the ribs 3 of the tray 1 with a correspondingly high speed.

It is additionally noted that due to the cleansing and sterilizing device that normally functions in a continuous manner, as well as the filling and closing device for the syringe bodies 2, both a first handling robot 40 with a device 10 for charging the conveying device and a second handling robot 40 or 40*a* with a device 10 or 10*a* for removing the filled syringe bodies 2 from the conveying device are required. With corresponding buffer zones in the conveying device, though, it is also conceivable to only use one handling robot 40, 40*a* with one device 10, 10*a*.

An apparatus modified in this way can, for example, be operated in such a way that in alternating fashion, one tray 1 is emptied by means of the device 10, 10*a* and then an empty tray 1 is filled with syringe bodies 2 by the same device 10, 10*a*.

Figure 7:
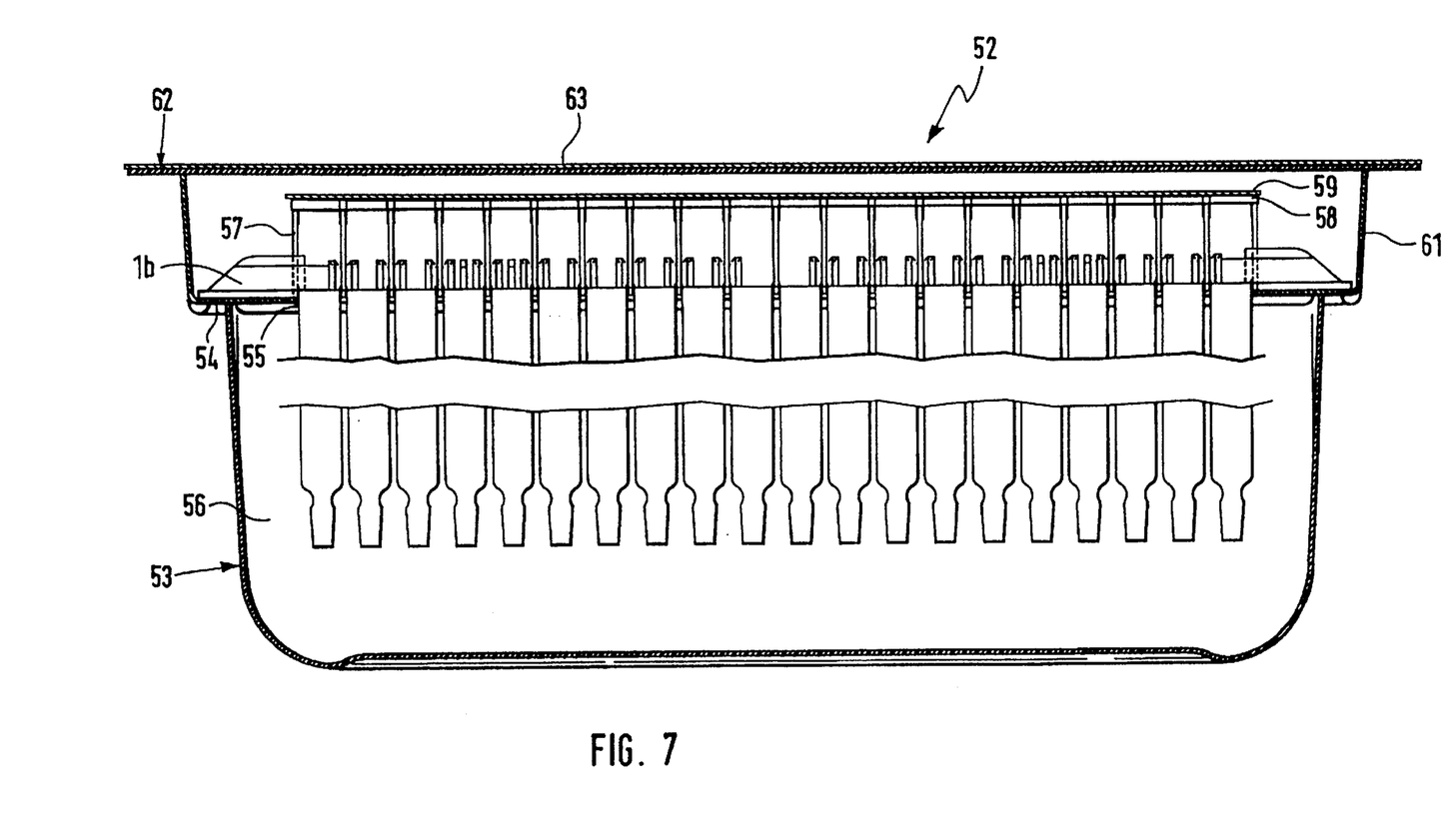
FIG. 7 shows a closed SCF system in a partially sectional side view.
Figure 8:
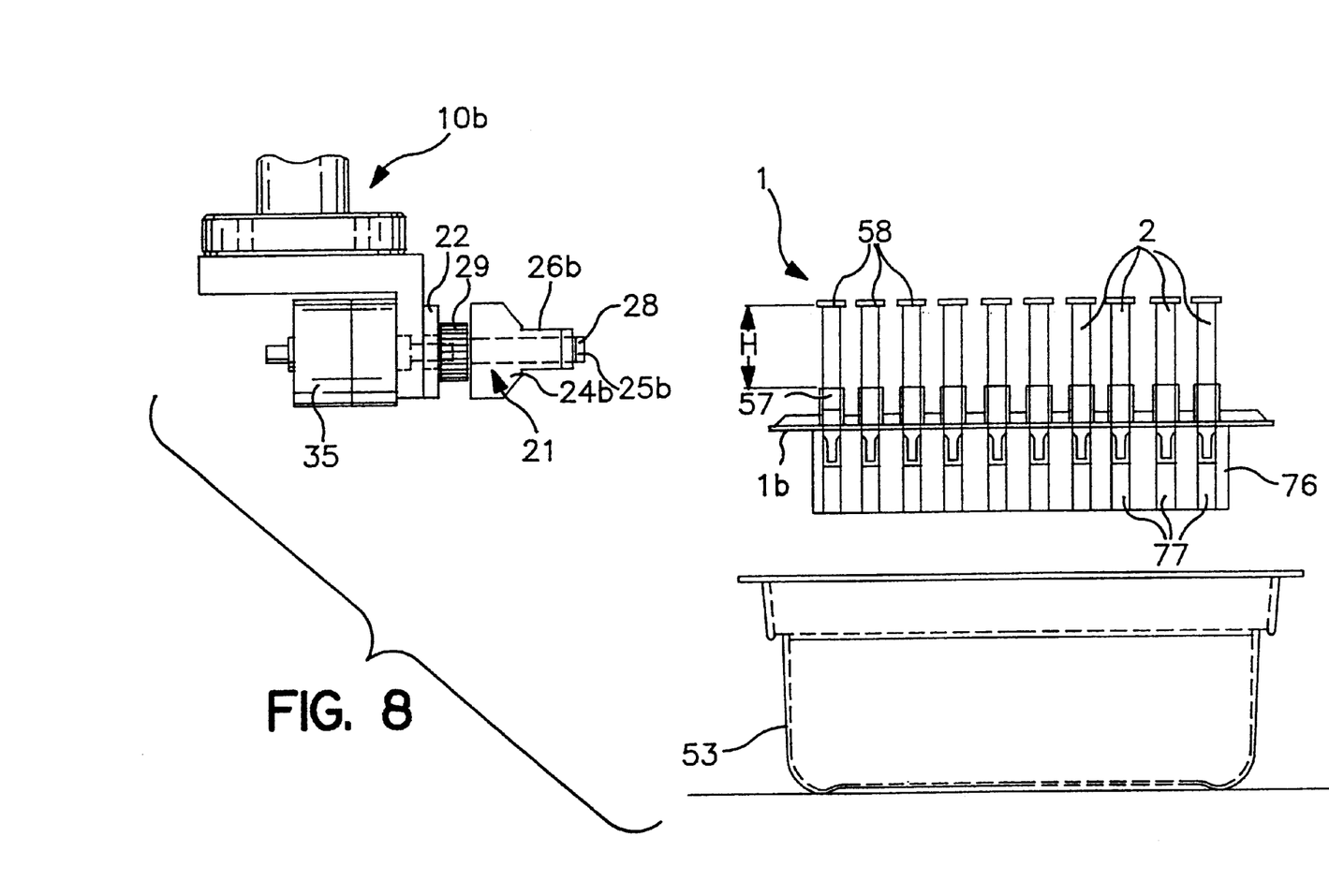
FIG. 8 is a side view of the handling of the SCF system according to FIG. 7.
Figure 9:
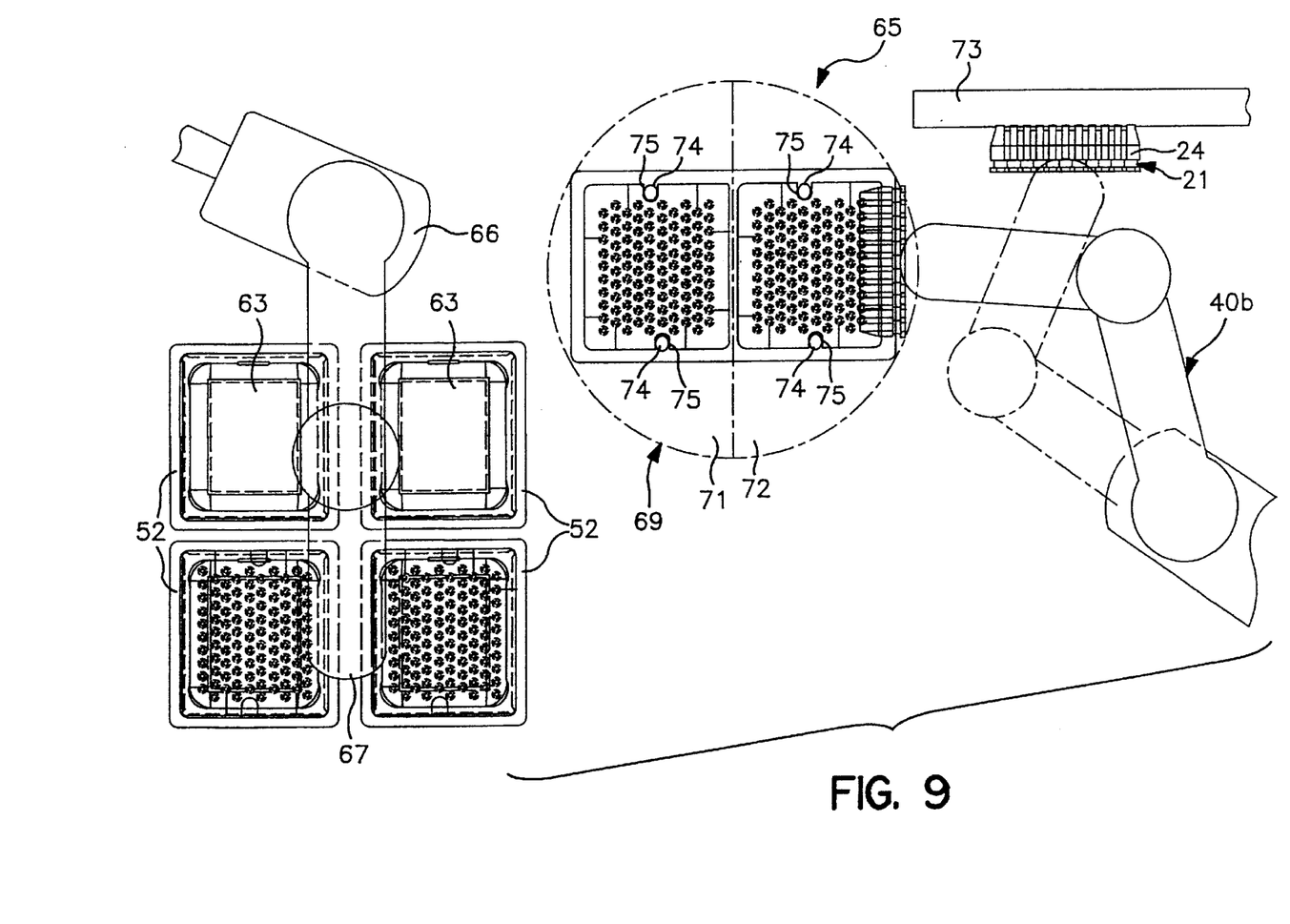
FIG. 9 is a top view of the entry region of a packaging apparatus for SCF systems.

In the second exemplary embodiment of the invention represented in FIGS. 7 to 9, the device 10*b* is used to handle syringe bodies 2 which are disposed in a so-called SCF system 52, which is used as a packaging container. The SCF system 52 has a tub-shaped container 53 that is preferably comprised of plastic. A continuous horizontal rim 54, on which a tray 1*b* rests in a sealed fashion, is embodied in the upper region of the container 53. The tray 1*b* that is likewise comprised of plastic has a number of rows of openings 55, which are disposed next to each other and one behind the other, each for a syringe body 2. On the top side of the tray 1*b*, which is remote from the sterile inner chamber 56 of the container 53, each opening 55 is associated with a syringe receiving sleeve 57 which is formed onto the tray 1*b*. The syringe receiving sleeves 57 encompass the syringe bodies 2 on their respective circumferences in a sealing and clamping manner. The syringe bodies 2 protrude so far into the inner chamber 56 of the container 53 that the flange-shaped continuous rim 58 embodied on the top side of the syringe bodies 2 rests against the top side of the syringe receiving sleeves 57. Consequently, the outer faces of the syringe bodies 2 that have been cleansed and sterilized at the syringe manufacturer are completely accommodated in a sterile manner in the inner chamber 56. In order to assure the sterility of the inner surfaces of the syringe bodies 2 as well, a sterile covering mat 59 that covers the syringe bodies 2 is disposed on the top side of the rims 58 of the syringe bodies 2. The above-described tray 1*b* is inserted all the way into the container 53, together with the syringe bodies 2 and the covering mat 59, and is closed there in an air tight manner. To this end, at the level of the syringe receiving sleeves 57, the container 53 has a continuous wall section 61 with an airtight protective foil 63 glued to its top side 62.

The SCF systems 52 of this kind that are produced at the syringe manufacturer, arrive at the filler in a preparation and transfer region 65 represented in FIG. 9. This region has sterile room conditions, for example, in accordance with the clean room class 100. A robot 66, which is known per se and has a gripper 67, is disposed in the preparation and transfer region 65 and opens the prepared SCF systems 52 by automatically removing the protective foil 63 and the covering mat 59. After this has been done, the robot 66 transfers the container 53 to an indexing table 69.

The indexing table 69, which can be rotated around a vertical axis, has a storage area 71 and a working area 72, each for one container 53. The containers 53 that have been prepared by the robot 66 are set down in the storage area 71 in order to arrive in the working area 72 after a rotation by 180 degrees. In the working area 72, the syringe bodies 2 are withdrawn from the container 53 and the tray 1*b* by the handling robot 40*b* as further described below, and are transferred to a schematically represented transport device 73. The transfer position of the handling robot 40*b* to the transfer unit 73 is drawn in dashed lines in FIG. 9.

In SCF systems 52, the device 10*b* used to handle the syringe bodies 2 preferably differs from the devices 10, 10*a* used in the first exemplary embodiment of the invention by means of a simplified construction. In particular, the pivoting and rotating device 20, the matrix 11 together with the press struts 15, the lifting units 18, and the base carrier 19 can be eliminated, as represented in FIG. 8.

The indexing table 69 has lifting elements 74 for removing the syringe bodies 2 from the container 53, of which each lifting element 74 engages in a recess 75 of the container 53 embodied on the top side 62 of the wall section 61 and thus lifts the tray 1b out from the container 53. Then, the tray 1b is lowered onto a syringe matrix 76. The syringe matrix 76 has a conically embodied centering bore 77 for each syringe body 2. After the syringe bodies 2 have dipped into the centering bores 77 by a certain amount due to the lowering of the tray 1b, the syringe bodies 2 are lifted out of the tray 1b as the tray 1b is lowered further, until their rims 58 protrude above the syringe receiving sleeves 57 by a quantity H. In this position of the syringe bodies 2, in which they are still guided in the syringe receiving sleeves 57, the row of syringe bodies 2 oriented toward the syringe body carrier 24b of the device 10b can be removed from the tray 1b. To that end, the syringe body carrier 24b moves with its recesses 25b, as shown in FIG. 8, against the syringe bodies 2, which are fixed in the recesses 25b after the rotation of the closing elements 26b. After this, the transfer of the syringe bodies 2 to the transport device 73 occurs in a known manner. Then, all the rows of the syringe bodies 2 are removed from the tray 1b by the device 10b in the above-described manner.

The reintroduction of the syringe bodies 2 into an empty tray 1b after the filling of the syringe bodies 2 is carried out in a correspondingly reversed order.

In addition to the two described exemplary embodiments, it is also conceivable to use the device 10, 10a, 10b according to the invention with other objects or packages. At any rate, the use is not limited to syringe bodies 2 disposed in trays 1, 1b, but after a corresponding modification, can be transferred to other industrial applications, in particular to a narrow division of vials, carpules, ampules and other cylindrical objects.

The foregoing relates to preferred exemplary embodiments of the invention, it being understood that other variants and embodiments thereof are possible within the spirit and scope of the invention, the latter being defined by the appended claims.

The invention claimed and desired to be secured by Letters Patent of the United States is:

1. A device (10, 10a, 10b) for handling syringe bodies (2) disposed between elastic securing ribs (3) of a packaging container (1, 1b), said device comprising a transfer unit (21), said transfer unit (21) includes a syringe body carrier (24), said syringe body carrier includes recesses (25) for receiving the syringe bodies and rotary closing elements for securing the syringe bodies to the transfer unit (21), said closing elements include, a plurality of rotatable securing elements (27) for securing the syringe bodies (2) in the recesses of said transfer unit (21), the securing elements (27) are rotatable so that in a first position of the securing elements (27), the recesses (25) are open for delivering or receiving the syringe bodies (2), and in a second position of the securing elements (27), the syringe bodies are capable of being grasped by the securing elements (27) for securing the syringe bodies within the recesses, the transfer unit (21) includes a matrix (11), adapted to be laid against the securing ribs (3) of the packaging container (1) for transferring the syringe bodies from the packaging container to the transfer unit (21), and that the transfer unit (21) and the matrix (11) are moved against one another in a direction of the packaging container (1) for transfer of the syringe bodies.

2. The device according to claim 1, in which the securing elements (27) are essentially disposed inside the transfer unit (21) and have securing catches (28) for grasping the syringe bodies (2) when the securing elements (27) are rotated.

3. The device according to claim 2, in which the matrix (11) has a recess (12) through which the rotary closing elements protrude.

4. The device according to claim 2, in which on the matrix (11), which is essentially plate-shaped, a number of spacer bodies (15) are disposed which coincide with the securing ribs (3) of the packaging container (1).

5. The device according to claim 2, in which the device (10) is connected to a handling robot (40).

6. The device according to claim 1, in which the matrix (11) has a recess (12) through which the transfer unit (21) protrudes.

7. The device according to claim 6, in which on the matrix (11), which is essentially plate-shaped, a number of spacer bodies (15) are disposed which coincide with the securing ribs (3) of the packaging container (1).

8. The device according to claim 6, in which the device (10) is connected to a handling robot (40).

9. The device according to claim 1, in which the matrix (11) is essentially plate-shaped, and on an end oriented toward the packaging container (1) contains a number of spacer bodies (15) which coincide with the securing ribs (3) of the packaging container (1).

10. The device according to claim 9, in which some of the spacer bodies (15) have different lengths (L).

11. The device according to claim 10, in which at least one suction bore (38) is formed in the spacer bodies (15) and is connected to a vacuum source.

12. The device according to claim 10, in which the device (10) is connected to a handling robot (40).

13. The device according to claim 9, in which at least one suction bore (38) is formed in the spacer bodies (15) and is connected to a vacuum source.

14. The device according to claim 13, in which the device (10) is connected to a handling robot (40).

15. The device according to claim 9, in which the device (10) is connected to a handling robot (40).

16. The device according to claim 1, in which the device (10) is connected to a handling robot (40).

* * * * *